United States Patent
Mankoo

(10) Patent No.: US 6,197,288 B1
(45) Date of Patent: *Mar. 6, 2001

(54) MALODOR COUNTERACTANT COMPOSITIONS AND METHOD FOR PREPARING AND USING SAME

(75) Inventor: Amrit Singh Mankoo, New Hampton, NY (US)

(73) Assignee: Bush Boake Allen, Inc., Montvale, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/951,784

(22) Filed: Oct. 16, 1997

(51) Int. Cl.$^7$ ................................. A61L 9/01; A61K 9/68
(52) U.S. Cl. ........................ 424/76.1; 424/48; 424/76.1; 424/76.21; 424/76.4; 424/439; 424/440; 424/441; 424/49; 514/974
(58) Field of Search ............... 424/48, 49, 76.1, 424/76.21, 76.4, 439, 440, 441; 514/974

(56) References Cited

U.S. PATENT DOCUMENTS

| | | | |
|---|---|---|---|
| 3,914,227 | * 10/1975 | Pittet et al. | 260/250 |
| 4,906,488 | * 3/1990 | Pera | 426/573 |
| 5,589,158 | * 12/1996 | Mankoo | 424/49 |

* cited by examiner

Primary Examiner—Thurman K. Page
Assistant Examiner—Lakshmi Channavajjala
(74) Attorney, Agent, or Firm—Richard R. Muccino

(57) ABSTRACT

This invention pertains to a malodor counteractant composition comprising a malodor counteractant agent in an oral vehicle. The malodor counteractant agent is selected from the group consisting of, in percentages by weight: (A) (a) geranyl propionate; (b) benzyl benzoate; and (c) neryl acetate; (B) (a) citronellyl acetate; (b) benzyl benzoate; and (c) neryl acetate; (C) (a) benzyl benzoate; (b) geranyl propionate; and (c) citronellyl acetate; (D) (a) geranyl propionate; (b) citronellyl acetate; and (c) benzyl benzoate; (E) (a) citronellyl acetate; and (b) geranyl propionate; (F) (a) benzyl benzoate; and (b) neryl acetate; (G) (a) benzyl benzoate; (b) neryl acetate; (c) trimethyl (2,6,6) vinyl(6) tetrahydropyran; (d) citronella oil; and (e) and ethyl alcohol; and (H) (a) benzyl benzoate; (b) neryl acetate; (c) citronella oil; (d) geranyl acetate; (e) alpha ionone; (f) geranyl propionate; (g) linalool; and (e) and ethyl alcohol. The malodor counteractant compositions may be used in a wide variety of oral vehicles such as chewing gum compositions, hard and soft confections, mouth washes and sprays, breath freshening drops and powdered mouthwashes, tooth pastes and powders, denture cleaners and adhesives, and dental floss.

4 Claims, No Drawings

MALODOR COUNTERACTANT COMPOSITIONS AND METHOD FOR PREPARING AND USING SAME

BACKGROUND OF THE INVENTION

1. Field of the Invention

This invention pertains to malodor counteractant compositions comprising an organoleptically effective amount of a malodor counteractant agent in an oral vehicle. The malodor counteractant agent is selected from the group consisting of (A) amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin; (B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and (C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin. The malodor counteractant compositions may be used in a wide variety of oral vehicles such as chewing gum compositions, hard and soft confections, mouth washes and sprays, breath freshening drops and powdered mouthwashes, tooth pastes and powders, denture cleaners and adhesives, and dental floss.

2. Description of the Background

A wide variety of breath freshener compositions have been developed to freshen breath that is offensive to the sense of smell. Particularly unpleasant odors are caused by compounds which have the ability to donate or accept protons such as lower carboxylic acids, thiols, thiophenols, phenols, lower amines, phosphines, and arsines. Compounds of this type that have unpleasant odors are known as malodor compounds and include isovaleric acid (rancid cheese odor), 3-methyl-1H-indole (skatole, fecal odor), and tert-butyl mercaptan (heavy skunk odor).

Conventional breath fresheners include a variety of fragrance materials that provide a pleasant perfume that masks the malodor compound generally by one of two mechanisms. In the first mechanism, the masking fragrance blends with the malodor compound to provide a different and more desirable aroma. In the second mechanism, the masking fragrance is employed in a large quantity to overwhelm the malodor compound.

Unfortunately both types of breath freshening mechanisms have serious disadvantages. Neither breath freshener completely eliminates the perception of malodor and so there is a tendency to use increasing amounts of the breath freshener to completely eliminate the perception of malodor. Furthermore, the masking effect is an additive effect and so the total odor level in the freshened breath is increased by consumption of the breath freshener. Even though the fragrances used in the breath freshener may be very pleasant at low concentration, the total odor level in the breath at the relatively high concentrations required to achieve moderate masking of the malodor may itself be offensive.

U.S. Pat. No. 4,622,221 (Schleppnik) discloses a method of counteracting a malodor in air. The method comprises introducing into the air an effective amount of cyclohexyl-1-ethyl-n-butyrate, and derivatives thereof.

U.S. Pat. No. 5,589,158 (Mankoo) discloses a flavor enhancing composition comprising between about 30% and 90% by weight benzyl benzoate and between about 3% and 15% by weight neryl acetate.

European patent application no. 0 251 542 (Lion Corporation) discloses an oral composition comprising a zinc salt and 0.1% to 5% by weight of polyoxyethylene hydrogenated castor oil.

Canadian patent no. 987,597 (McNamara et al.) discloses compositions having odor masking properties. The compositions comprise a reodorant compound selected from the group consisting of α-ionone, α-methyl ionone, citral, geranyl formate, and geranyl acetate. The reodorant compounds are used in an amount from 50 to 3000 parts per million, by weight.

While the above compositions provide some degree of air or breath freshening action, none of the above compositions are satisfactory malodor counteractant compositions. The present invention provides malodor counteractant compositions without the disadvantages which are characteristic of previously known products. The present invention also provides methods for preparing and using these malodor counteractant compositions and the compositions in which they may be employed. The malodor counteractant compositions may be used in a wide variety of oral vehicles.

SUMMARY OF THE INVENTION

The present invention is a directed at a malodor counteractant composition comprising an organoleptically effective amount of a malodor counteractant agent in an oral vehicle. The malodor counteractant agent is selected from the group consisting of:

(A) amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin;

(B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and (C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin.

In one embodiment, the malodor counteractant agent is selected from the group consisting of amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, and vanillin. In another embodiment, the malodor counteractant agent is selected from the group consisting of amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, and phenyl ethyl alcohol. In yet another embodiment, the malodor counteractant agent is selected from the group consisting of amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, and vanillin.

In a most preferred embodiment, the malodor counteractant composition comprises in percentages by weight (a) benzyl benzoate in an amount of about 30%; (b) neryl acetate in an amount of about 7.5%; (c) trimethyl(2,6,6) vinyl(6) tetrahydropyran in an amount of about 0.10%; (d) citronella oil in an amount of about 0.10%; and (e) and ethyl alcohol in an amount of about 62.30%. In another most preferred embodiment, the malodor counteractant composition comprises in percentages by weight (a) benzyl benzoate in an amount of about 30%; (b) neryl acetate in an amount of about 7.0%; (c) citronella oil in an amount of about 0.10%; (d) geranyl acetate in an amount of about 0.10%; (e) alpha ionone in an amount of about 0.10%; (f) geranyl propionate in an amount of about 0.05%; (g) linalool in an amount of about 0.02%; and (e) and ethyl alcohol in an amount of about 62.63%.

The malodor counteractant compositions may further comprise an organoleptically acceptable solvent. The malodor counteractant compositions may be used in a wide variety of oral vehicles such as chewing gum compositions, hard and soft confections, mouth washes and sprays, breath freshening drops and powdered mouthwashes, tooth pastes and powders, denture cleaners and adhesives, and dental floss. The malodor counteractant compositions may also be used in a wide variety of nonoral vehicles such as for use in pet foods. The present invention also pertains to methods for preparing and using the malodor counteractant compositions and the oral products in which they may be used.

DETAILED DESCRIPTION OF THE INVENTION

The present invention relates to malodor counteractant compositions comprising an organoleptically effective amount of a malodor counteractant agent in an oral vehicle. Typical malodor compounds include lower aliphatic carboxylic acids, lower aliphatic amines, and sulfur compounds such as $H_2S$, lower aliphatic mercaptans, aromatic mercaptans, and dimethy sulfides. Applicant has discovered malodor counteractant agents that reduce or eliminate the perception of malodor without increasing the total odor level. Unlike odor masking agents, which increase the overall odor level without eliminating the perception of the odor, malodor counteractant agents abate a given malodor while reducing the combined intensity of the odor level. Applicant believes that the malodor counteractant agents counteract the perception of malodors because the counteractant agents bind to the same receptor sites in the nose as the malodor compounds. Applicant believes that the malodor counteractant agents competitively interact and bind with proteins at the receptor sites and thereby render the sites unavailable to malodor compounds. The malodor counteractant agents may further comprise an organoleptically acceptable solvent such as propylene glycol, ethanol, triacetin, glycerol, and vegetable oils. The malodor counteractant agents may be used in a wide variety of oral vehicles such as chewing gum compositions, hard and soft confections, mouth washes. tooth pastes, denture cleaners, and dental floss.

The following terms are used throughout the specification and are defined as follows unless otherwise indicated.

The terms "ingestible" and "edible", as used herein, refer to all materials and compositions which are used by or which perform a function in the body. These materials and compositions include those which are adsorbed and those which are not absorbed as well as those which are digestible and non-digestible.

The terms "flavor", "flavoring", and "flavorant", as used herein, are used interchangeably whenever an organoleptic compound is referred to which is intended to stimulate the sense of taste and smell.

The term "organoleptic", as used herein, refers to compounds of the invention which stimulate the sense of smell or taste, and are thus perceived as having a characteristic odor and/or flavor. The term "organoleptically acceptable solvent", as used herein, refers to solvents which do not stimulate the sense of smell or taste, and are thus perceived as not having a characteristic odor and/or flavor. The term "organoleptically effective amount", as used herein, means a level or amount of flavoring compound(s) present in a material at which the incorporated compound(s) exhibit(s) a sensory effect.

In accord with the present invention, the malodor counteractant compositions comprise an organoleptically effective amount of a malodor counteractant agent in an oral vehicle. The malodor counteractant agent is selected from the group consisting of (A) amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin; (B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and (C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin.

In a preferred embodiment, the malodor counteractant agent is selected from the group consisting of amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, and vanillin. In another preferred embodiment, the malodor counteractant agent is selected from the group consisting of amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, and phenyl ethyl alcohol. In another preferred embodiment, the malodor counteractant agent is selected from the group consisting of amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, and vanillin.

In a more preferred embodiment, the malodor counteractant agent is selected from the group consisting of amyl cinnamic aldehyde, benzyl benzoate, dimethyl benzyl carbinol, dimethyl benzyl carbinyl acetate, geranyl isovalerate, hexyl cinnamic aldehyde, isobornyl acetate, nerol, neryl acetate, and phenyl ethyl isovalerate. In another more preferred embodiment, the malodor counteractant agent is citronellyl acetate or geranyl propionate.

In a most preferred embodiment, the malodor counteractant composition comprises in percentages by weight (a) geranyl propionate in an amount from about 85% to about 99.99%; (b) benzyl benzoate in an amount from about 0.001% to about 10%; and (c) neryl acetate in an amount from about 0.001% to about 10%. In another most preferred embodiment, the malodor counteractant composition comprises in percentages by weight (a) citronellyl acetate in an amount from about 85% to about 99.99%; (b) benzyl benzoate in an amount from about 0.001% to about 10%; and (c) neryl acetate in an amount from about 0.001% to about 10%. In another most preferred embodiment, the malodor counteractant composition comprises in percentages by weight (a) benzyl benzoate in an amount from about 70% to about 95%; (b) geranyl propionate in an amount from about 3% to about 20%; and (c) citronellyl acetate in an amount from about 1% to about 15%. In another most preferred embodiment, the malodor counteractant composition comprises in percentages by weight (a) geranyl propionate in an amount from about 65% to about 85%; (b) citronellyl acetate in an amount from about 10% to about 25%; and (c) benzyl benzoate in an amount from about 1% to about 15%. In another most preferred embodiment, the malodor counteractant composition comprises in percentages by weight (a) citronellyl acetate in an amount from about 55% to about 75%; and (b) geranyl propionate in an amount from about 25% to about 45%. In another most preferred embodiment, the malodor counteractant composition comprises in percentages by weight (a) benzyl benzoate in an amount from about 75% to about 85%; and (b) neryl acetate in an amount from about 15% to about 25%. In another most preferred embodiment, the malodor counteractant composition comprises in percentages by weight (a) benzyl benzoate in an amount of about 30%; (b) neryl acetate in an amount of about 7.5%; (c) trimethyl(2,6,6) vinyl(6) tetrahydropyran in an amount of about 0.10%; (d) citronella oil in an amount of about 0.10%; and (e) and ethyl alcohol in an amount of about 62.30%. In another most preferred embodiment, the malodor counteractant composition comprises in percentages by weight (a) benzyl benzoate in an amount of about 30%; (b) neryl acetate in an amount of about 7.0%; (c) citronella oil in an amount of about 0.10%; (d) geranyl acetate in an amount of about 0.10%; (e) alpha ionone in an amount of about 0.10%; (f) geranyl propionate in an amount of about 0.05%; (g) linalool in an amount of about 0.02%; and (e) and ethyl alcohol in an amount of about 62.63%.

The malodor counteractant agents of the present invention may be used in many distinct physical forms well known in the pharmaceutical art to provide an initial dosage of the malodor counteractant agent and/or a further time-release form of the malodor counteractant agent. Without being limited thereto, such physical forms include free forms and encapsulated forms, and mixtures thereof.

The amount of the inventive malodor counteractant agent employed in an oral composition is an organoleptically effective amount to provide a malodor counteractant composition that abates a given malodor while reducing the combined intensity of the odor level. The exact amount of malodor counteractant agent used may vary depending upon the type of malodor counteractancy agent employed, the type of oral vehicle employed, and the level of malodor counteractancy desired. In general, the amount of malodor counteractant agent present is the ordinary dosage required to obtain the desired result. Such dosages are known to the skilled practitioner in the confectionery arts and are not a part of the present invention. In a preferred embodiment, the malodor counteractant agent in the malodor counteractant composition is present in an amount from about 0.0001% to about 10%, preferably from about 0.001% to about 5%, and more preferably from about 0.01% to about 2%, by weight.

The malodor counteractant agents may be used in a wide variety of oral vehicles. Nonlimiting examples of suitable oral vehicles include chewing gum compositions, hard and soft confections, mouth washes, tooth pastes, denture cleaners, and dental floss. The combination of the malodor counteractant agent of the present invention together with an oral vehicle and optional ingredients, when desired, provides a malodor counteractant composition that abates a given malodor while reducing the combined intensity of the odor level.

The malodor counteractant compositions may further comprise an organoleptically acceptable solvent. The organoleptically acceptable solvent may be any solvent which does not interfere with the organoleptic properties of the malodor counteractant compositions of the present invention. In general, the organoleptically acceptable solvent does not stimulate the sense of smell or taste, and is not perceived as having a characteristic odor and/or flavor. Illustrative nonlimiting examples of organoleptically acceptable solvents may be selected from the group consisting of propylene glycol, ethanol, triacetin, glycerol, and vegetable oils. When employed, the organoleptically acceptable solvent will be present in an amount from about 1% to about 75%, preferably from about 2% to about 50%, and more preferably from about 5% to about 25%, by weight.

The present invention extends to methods for preparing the malodor counteractant compositions. In such a method, the malodor counteractant composition is prepared by admixing one or more malodor counteractant agent in an oral vehicle, together with any optional ingredients, to form a uniform mixture. The final compositions are readily prepared using standard methods and apparatus generally known by those skilled in the confectionery arts. The apparatus useful in accordance with the present invention comprises mixing apparatus well known in the confectionery arts, and therefore the selection of the specific apparatus will be apparent to the artisan.

In a specific embodiment, the present invention is directed to a method for making a malodor counteractant composition which comprises admixing an organoleptically effective amount of a malodor counteractant agent with an oral vehicle, wherein the malodor counteractant agent is selected from the group consisting of:

(A) amyl cinnamic aldehyde, beizyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin;

(B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and (C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin.

In another embodiment, the present invention is directed at a method for using a malodor counteractant composition that abates a malodor while reducing the combined intensity of the odor level which comprises (a) admixing an organoleptically effective amount of a malodor counteractant agent and an oral vehicle to form a malodor counteractant composition; and (b) administering the malodor counteractant composition to a mammal.

An important aspect of the present invention includes an improved chewing gum composition incorporating the inventive malodor counteractant agent and a method for preparing the chewing gum composition, including both chewing gum and bubble gum formulations. In general, the improved chewing gum compositions will contain a gum base, a bulking agent, an organoleptically effective amount of a malodor counteractant agent, and various additives such as a flavoring agent.

The chewing gum compositions may be reduced-calorie chewing gums employing high levels of a chewing gum base having an enhanced hydrophilic character. These reduced-calorie chewing gums will comprise a gum base present in an amount from about 50% to about 85%, preferably from about 50% to about 75%, and more preferably from about 60% to about 70%, by weight of the chewing gum composition. When a reduced-calorie product is not desired, the chewing gum composition may contain lower amounts of a chewing gum base. These chewing gums will comprise a gum base present in an amount up to about 55%, preferably from about 15% to about 40%, and more preferably from about 20% to about 35%, by weight of the chewing gum composition.

As used herein, the term "reduced-calorie composition" means a composition having a caloric value two thirds or less than that of a conventional composition. The term "tight" or "rubbery" chew refers to a chewing gum composition which requires a large amount of muscular chewing effort to masticate or to a composition which provides a gum bolus with high elasticity and bounce and which is difficult to deform.

Gum bases having an enhanced hydrophilic character include polyvinyl acetate gum bases which may also contain a low melting point wax. Such gum bases do not require a high level of bulking agent to plasticize the gum base and render it soft during chewing. These gum bases may be used at higher than normal levels in chewing gum compositions in place of a bulking and/or a bulk sweetening agent to prepare high base-low bulking agent reduced-calorie gums which do not have rubbery or tight chew characteristics. These gum bases possess increased hydrophilic properties over conventional gum bases and appear to increase in size during chewing releasing flavoring and sweetening agents which would normally be entrapped in the gum base while maintaining a soft chew texture. Reduced-calorie chewing gum compositions prepared with such gum bases in high levels are less hygroscopic (have lower moisture-pickup) and are less prone to becoming stale than conventional reduced-calorie gum compositions while having comparable firmness and texture.

The elastomers (rubbers) employed in the gum base of the present invention will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, and the like, and mixtures thereof.

The amount of elastomer employed in the gum base will vary greatly depending upon various factors such as the type of gum base used, the consistency of the gum composition desired and the other components used in the composition to make the final chewing gum product. In general, the elastomer will be present in the gum base in an amount from about 0.5% to about 20%, and preferably from about 2.5 % to about 15%, by weight of the gum base.

The polyvinyl acetate polymer employed in the gum base of the present invention is a polyvinyl acetate polymer having a medium molecular weight, specifically, having a mean average molecular weight in the range from about 35,000 to about 55,000. This medium molecular weight polyvinyl acetate polymer will preferably have a viscosity from about 35 seconds to about 55 seconds (ASTM designation D1200-82 using a Ford cup viscometer procedure). The medium molecular weight polyvinyl acetate polymer will be present in the gum base in an amount from about 10% to about 25%, and preferably from about 12% to about 27%, by weight of the gum base.

The medium molecular weight polyvinyl acetate polymer may also be blended with a low molecular weight polyvinyl acetate polymer. The low molecular weight polyvinyl acetate polymer will have a mean average molecular weight in the range from about 12,000 to about 16,000. This low molecular weight polyvinyl acetate polymer will preferably have a viscosity from about 14 seconds to about 16 seconds (ASTM designation D1200-82 using a Ford cup viscometer procedure). The low molecular weight polyvinyl acetate polymer will be present in the gum base in an amount up about 17%, and preferably from about 12% to about 17%, by weight of the gum base.

When a low molecular weight polyvinyl acetate polymer is blended with a medium molecular weight polyvinyl acetate polymer, the polymers will be present in a mole ratio from about 1:0.5 to about 1:1.5, respectively.

The medium molecular weight polyvinyl acetate polymer may also be blended with a high molecular weight polyvinyl acetate polymer. The high molecular weight polyvinyl acetate polymer will have a mean average molecular weight in the range from about 65,000 to about 95,000. The high molecular weight polyvinyl acetate polymer will be present in the gum base in an amount up to about 5%, by weight of the gum base.

The acetylated monoglycerides in the present invention, like the polyvinyl acetate polymer, serve as plasticizing agents. While the saponification value of the acetylated monoglycerides is not critical, preferable saponification values are 278 to 292, 316 to 331, 370 to 380, and 430 to 470. A particularly preferred acetylated monoglyceride has a saponification value above about 400. Such acetylated monoglycerides generally have an acetylation value (percentage acetylated) above about 90 and a hydroxyl value below about 10 (Food Chemical Codex (FCC) III/P508 and the revision of AOCS).

The use of acetylated monoglycerides in the present gum base is preferred over the use of bitter polyvinyl acetate (PVA) plasticizers, in particular, triacetin. The acetylated monoglycerides will be present in the gum base in an amount from about 4.5% to about 10%, and preferably from about 5% to about 9%, by weight of the gum base.

The wax in the gum base of the present invention softens the polymeric elastomer mixture and improves the elasticity of the gum base. The waxes employed will have a melting point below about 60° C., and preferably between about 45° C. and about 55° C. A preferred wax is low melting paraffin wax. The wax will be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnauba wax, most petroleum waxes, and the like, and mixtures thereof.

In addition to the components set out above, the gum base includes a variety of traditional ingredients, such as a component selected from the group consisting of elastomer solvents, emulsifiers, plasticizers, fillers, and mixtures thereof. These ingredients are present in the gum base in an amount to bring the total amount of gum base to 100%.

The gum base may contain elastomer solvents to aid in softening the elastomer component. Such elastomer solvents may comprise those elastomer solvents known in the art, for example, terpinene resins such as polymers of alpha-pinene or beta-pinene, methyl, glycerol and pentaerythritol esters of rosins and modified rosins and gums, such as hydrogenated, dimerized and polymerized rosins, and mixtures thereof. Examples of elastomer solvents suitable for use herein include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 11%, by weight of the gum base.

The gum base may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. A preferred emulsifier is glyceryl monostearate. The emulsifier may be employed in amounts from about 2% to about 15%, and preferably from about 7% to about 11%, by weight of the gum base.

The gum base may also include plasticizers or softeners to provide a variety of desirable textures and consistency properties. Because of the low molecular weight of these ingredients, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20%, and preferably in amounts from about 9% to about 17%, by weight of the gum base.

Preferred plasticizers are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to about 14%, and preferably in amounts from about 5% to about 13.5%, by weight of the gum base.

In another preferred embodiment, the softening agent is anhydrous glycerin, such as the commercially available United States Pharmacopeia (USP) grade. Glycerin is a syrupy liquid with a sweet warm taste and has a sweetness of about 60% of that of cane sugar. Because glycerin is hygroscopic, it is important that the anhydrous glycerin be maintained under anhydrous conditions throughout the preparation of the chewing gum composition.

The gum base of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, and the like, and mixtures thereof. These fillers or adjuvants may be used in the gum base compositions in various amounts. Preferably the amount of filler, when used, will be present in an amount from about 15% to about 40%, and preferably from about 20% to about 30%, by weight of the gum base.

A variety of traditional ingredients may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the gum base.

The manner in which the gum base components are admixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. After blending is complete, the polyvinyl acetate component is admixed into the mixture. The medium molecular weight polyvinyl acetate is preferably admixed prior to addition of the optional low molecular weight polyvinyl acetate to prevent the creation of pockets of polyvinyl acetate within the elastomer mixture. The remaining ingredients, such as the low melting point wax, are then admixed, either in bulk or incrementally, while the gum base mixture is blended again for 1 to 30 minutes.

In one embodiment, the invention pertains to a reduced-calorie chewing gum composition which comprises a gum base present in an amount from about 40% to about 75%, by weight of the chewing gum composition, which comprises (a) an elastomer present in an amount from about 0.5% to about 20%, by weight of the gum base, (b) a medium molecular weight polyvinyl acetate polymer having a molecular weight from about 35,000 to about 55,000 present in a n amount from about 10% to about 25%, by weight of the gum base, (c) an acetylated monoglyceride present in an amount from about 4.5% to about 10%, by weight of the gum base, (d) a wax having a melting point below about 60° C. present in an amount from about 6% to about 10%, by weight of the gum base, and (e) a material selected from the group consisting of elastomer solvents, emulsifiers, plasticizers, fillers, and mixtures thereof, present in an amount to bring the total amount of gum base to 100%, by weight of the gum base.

Chewing gum compositions employing a high level of a chewing gum base having an enhanced hydrophilic character are more fully described in U.S. Pat. No. 4,872,884, which disclosure is incorporated herein by reference.

Other gum bases having an enhanced hydrophilic nature and suitable for use in reduced-calorie chewing gum compositions in high levels may also be employed in the present invention. In general, these gum bases may be employed in amounts up to 99%, preferably from about 40% to about 85%, and more preferably from about 40% to about 75%, by weight of the chewing gum composition. Suitable gum bases having an enhanced hydrophilic nature include, for example, those disclosed in U.S. Pat. No. 4,698,223, which disclosure is incorporated herein by reference. The gum base is formulated with the inventive malodor counteractant composition and conventional additives such as a bulking agent to prepare a wide variety of sweetened chewing gum compositions.

The amount of gum base employed in the chewing gum composition will vary depending on such factors as the type of gum base used, the consistency desired, and the other components used to make the final chewing gum product. In general, the gum base having an enhanced hydrophilic character will be present in the chewing gum composition in an amount from about 50% to about 85%, preferably from about 50% to about 75%, and more preferably from about 60% to about 70%, by weight of the chewing gum composition.

In another embodiment, the invention pertains to a chewing gum composition which contains lower amounts of a chewing gum base. In general, the gum base in these chewing gum compositions will be present in an amount up to about 55%, preferably from about 15% to about 40%, and more preferably from about 20% to about 35%, by weight of the chewing gum composition. In this embodiment, the gum base will comprise an elastomer and a variety of traditional ingredients such as an elastomer solvent, waxes, emulsifiers, plasticizers or softeners, bulking agents such as mineral adjuvants which may serve as fillers and textural agents, coloring agents, antioxidants, preservatives, flavoring agents, and the like, and mixtures thereof. Illustrative examples of these gum base components have been set out above.

Once prepared, the gum base may be formulated with the malodor counteractant agent of the present invention and conventional additives to prepare a wide variety of chewing gum compositions.

The chewing gum compositions generally include bulking agents. These bulking agents (carriers, extenders) may be water-soluble and include bulking agents selected from the group consisting of, but not limited to, monosaccharides, disaccharides, polysaccharides, sugar alcohols, and mixtures thereof; isomalt (a mixture of alpha-D-glucopyranosyl-1,6-mannitol and alpha-D-glucopyranosyl-1,6-sorbitol manufactured under the tradename Palatinit by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate, celluloses and the like, and mixtures thereof. Bulking agents may be used in amounts up to about 60%, and preferably in amounts from about 25% to about 60%, by weight of the chewing gum composition.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof. When the chewing gum composition is a sugar gum, mixtures of sucrose and corn syrup solids are the preferred sugar bulking agents.

Suitable sugar alcohol bulking agents include sorbitol, xylitol, mannitol, galactitol, maltitol, and mixtures thereof. Mixtures of sorbitol and mannitol are the preferred sugar alcohol bulking agents.

Maltitol is a sweet, non-caloric, water-soluble sugar alcohol useful as a bulking agent in the preparation of non-caloric beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

The chewing gum compositions may also include a high intensity sweetening agent (sweeteners). High intensity sweetening agents have a sweetness intensity substantially greater than that of sucrose. Suitable high intensity sweetening agents include water-soluble natural sweetening agents such as dihydrochalcones, monellin, Stevia Rebaudiana (steviosides), glycyrrhizin, and mixtures thereof. Suitable water-soluble artificial sweetening agents include saccharin and its soluble salts, i.e., sodium and calcium saccharin salts, cyclamate and its salts, 3,4-dihydro-6-methyl-1,2,3-oxathiazine-4-one-2,2-dioxide (Acesulfame) and the sodium, ammonium, and calcium salts thereof, and especially the potassium salt of 3,4-dihydro-6-methyl-1,2,3-oxathiazine-4-one-2,2-dioxide (Acesulfame-K).

Suitable dipeptide based sweetening agents include L-aspartic acid derived sweetening agents such as L-aspartyl-L-phenylalanine methyl ester (Aspartame), compounds described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenylglycine, L-aspartyl-2,5-dihydro-L-phenyl-alanine, and L-aspartyl-L-(1-cyclohexen)alanine.

Other suitable water-soluble sweetening agents include those derived from naturally occurring water-soluble sweetening agents such as chlorinated derivatives of sucrose, e.g., chlorodeoxysugar derivatives such as derivatives of chlorodeoxysucrose and chlorodeoxy-galactosucrose. Examples of chlorodeoxysucrose and chlorodeoxygalactosucrose derivatives include but are not limited to 1-chloro-1'-deoxysucrose; 4-chloro-4-deoxy-alpha-D-galacto-pyranosyl-alpha-D-fructofuranoside, or 4-chloro-4-deoxygalactosucrose; 4-chloro-4-deoxy-alpha-D-galacto-pyranosyl-1-chloro-1-deoxy-beta-D-fructo-furanoside, or 4,1'-dichloro-4,1'-dideoxygalactosucrose; 1',6'-dichloro-1',6'-dideoxysucrose; 4-chloro-4-deoxy-alpha-D-galacto-pyranosyl-1,6-dichloro-1,6-dideoxy-beta-D-fructo-furanoside, or 4,1',6'-trichloro-4,1',6'-trideoxygalacto-sucrose; 4,6-dichloro-4,6-dideoxy-alpha-D-galacto-pyranosyl-6-chloro-6-deoxy-beta-D-fructo-furanoside, or 4,6,6'-trichloro-4,6,6'-trideoxygalacto-sucrose; 6,1',6'-trichloro-6,1',6'-trideoxysucrose; 4,6-dichloro-4,6-dideoxy-alpha-D-galacto-pyranosyl-1,6-dichloro-1,6-di-deoxy-beta-D-fructofuranoside, or 4,6,1',6'-tetrachloro-4,6,1',6'-tetradeoxygalacto-sucrose; and 4,6,1',6'-tetrachloro-4,6,1',6'-tetradeoxy-sucrose. In a preferred embodiment, the chlorodeoxysugar derivative is 4,1',6'-trichloro-4,1',6'-trideoxygalacto-sucrose, or 4-chloro-4-deoxy-alpha-D-galactopyranosyl-1,6-dichloro-1,6-dideoxy-beta-D-fructofuranoside, which is commercially available under the tradename Sucralose from McNeil Specialty Products Company, Skillman, N.J.

Other suitable high intensity sweetening agents include protein based sweetening agents such as talin (*Thaumatococcous danielli,* Thaumatin I and II).

The amount of the high intensity sweetening agent employed in the chewing gum composition is an effective amount to sweeten the chewing gum. In general, the amount of high intensity sweetening agent normally present in a chewing gum composition will be from about 0.001% to about 1%, preferably from about 0.01% to about 1%, and more preferably from about 0.05% to about 0.5%, by weight of the chewing gum composition.

The gum composition may include effective amounts of conventional additives selected from the group consisting of plasticizers, softeners, emulsifiers, waxes, fillers, mineral adjuvants, flavoring agents (flavors, flavorings), coloring agents (colorants, colorings), antioxidants, acidulants, thickening agents, and the like, and mixtures thereof. These ingredients are present in the chewing gum composition in an amount to bring the total amount of chewing gum composition to 100%. Some of these additives may serve more than one purpose. For example, in sugarless gum compositions, a sweetening agent, such as sorbitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickening agents, used alone or in combination with other softeners, such as methyl cellulose, alginates, carrageenan, xanthan gum, gelatin, carob, tragacanth, and locust bean, acidulants such as malic acid, adipic acid, citric acid, tartaric acid, fumaric acid, and mixtures thereof, and fillers, such as those discussed above under the category of mineral adjuvants.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include vanilla, spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are natural and synthetic fruit flavors such as citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63–258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (citrus fruits such as orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well known and do not constitute a part of this invention.

The flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof.

Encapsulated delivery systems for flavoring agents or sweetening agents comprise a hydrophobic matrix of fat or wax surrounding a sweetening agent or flavoring agent core. The fats may be selected from any number of conventional materials such as fatty acids, glycerides or polyglycerol esters, sorbitol esters, and mixtures thereof. Examples of fatty acids include hydrogenated and partially hydrogenated vegetable oils such as palm oil, palm kernel oil, peanut oil, rapeseed oil, rice bran oil, soybean oil, cottonseed oil, sunflower oil, safflower oil, and mixtures thereof. Glycerides which are useful include monoglycerides, diglycerides, and triglycerides.

Waxes useful may be chosen from the group consisting of natural and synthetic waxes, and mixtures thereof. Non-limiting examples include paraffin wax, petrolatum, carbowax, microcrystalline wax, beeswax, carnauba wax, candellila wax, lanolin, bayberry wax, sugarcane wax, spermaceti wax, rice bran wax, and mixtures thereof.

The fats and waxes may be use individually or in combination in amounts varying from about 10 to about 70%, and preferably in amounts from about 40 to about 58%, by weight of the encapsulated system. When used in combination, the fat and wax are preferably present in a ratio from about 70:10 to 85:15, respectively.

Typical encapsulated flavoring agent or sweetening agent delivery systems are disclosed in U.S. Pat. Nos. 4,597,970 and 4,722,845, which disclosures are incorporated herein by reference.

The amount of flavoring agent employed herein is normally a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5%, and preferably from about 0.1% to about 2%, and more preferably, from about 0.8% to about 1.8%, by weight of the chewing gum composition.

The coloring agents useful in the present invention are used in amounts effective to produce the desired color. These coloring agents include pigments which may be incorporated in amounts up to about 6%, by weight of the gum composition. A preferred pigment, titanium dioxide, may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5'-indigotindisulfonic acid. Similarly, the dye known as F.D.& C. Green No.1 comprises a triphenylmethane dye and is the disodium salt of 4-[4-(N-ethyl-p-sulfoniumbenzylamino) diphenylmethylene]-[1-(N-ethyl-N-p-sulfoniumbenzyl)-delta-2,5-cyclohexadienimine]. A full recitation of all F.D.& C. colorants and their corresponding chemical structures may be found in the Kirk-Othmer Encyclopedia of Chemical Technology, 3rd Edition, in volume 5 at pages 857–884, which text is incorporated herein by reference.

Suitable oils and fats usable in gum compositions include partially hydrogenated vegetable or animal fats, such as coconut oil, palm kernel oil, beef tallow, lard, and the like. These ingredients when used are generally present in amounts up to about 7%, and preferably up to about 3.5%, by weight of the gum composition.

In accordance with this invention, organoleptically effective amounts of the malodor counteractant agent of the present invention may be admixed into the chewing gum composition. The exact amount of malodor counteractant agent employed is normally a matter of preference subject to such factors as the particular type of gum composition being prepared, the type of bulking agent employed, the type of flavor employed, and the intensity of breath freshening perception desired. Thus, the amount of malodor counteractant agent may be varied in order to obtain the result desired in the final product and such variations are within the capabilities of those skilled in the art without the need for undue experimentation. In general, the amount of malodor counteractant agent normally present in a chewing gum composition will be from about 0.01% to about 2%, preferably from about 0.1% to about 2%, and more preferably from about 0.25% to about 2%, by weight of the chewing gum composition.

In a preferred embodiment, the present invention is directed to a chewing gum composition comprising:

(i) a gum base;

(ii) a bulking agent; and (iii) an organoleptically effective amount of a malodor counteractant agent selected from the group consisting of:

(A) amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin;

(B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and (C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin.

The present invention also includes a method for preparing the improved chewing gum compositions, including both chewing gum and bubble gum formulations. The chewing gum compositions may be prepared using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

In such a method, a chewing gum composition is made by admixing the gum base with the malodor counteractant agent and the other ingredients of the final desired chewing gum composition. Other ingredients will usually be incorporated into the composition as dictated by the nature of the desired composition as well known by those having ordinary skill in the art. The ultimate chewing gum compositions are readily prepared using methods generally known in the food technology and chewing gum arts.

For example, the gum base is heated to a temperature sufficiently high to soften the base without adversely effecting the physical and chemical make up of the base. The optimal temperatures utilized may vary depending upon the composition of the gum base used, but such temperatures are readily determined by those skilled in the art without undue experimentation.

The gum base is conventionally melted at temperatures that range from about 60° C. to about 120° C. for a period of time sufficient to render the base molten. For example, the gum base may be heated under these conditions for a period of about thirty minutes just prior to being admixed incrementally with the remaining ingredients of the gum composition such as the inventive malodor counteractant agent, plasticizer, the softener, the bulking agent, and/or fillers, coloring agents and flavoring agents to plasticize the blend as well as to modulate the hardness, viscoelasticity and formability of the base. Mixing is continued until a uniform mixture of gum composition is obtained. Thereafter the gum composition mixture may be formed into desirable chewing gum shapes.

In a preferred embodiment, the invention is directed at a method for preparing a chewing gum composition which comprises the steps of:

(1) providing the following ingredients:
    (i) a gum base;
    (ii) a bulking agent; and
    (iii) an organoleptically effective amount of a malodor counteractant agent;
(2) melting the gum base;
(3) admixing the bulking agent and the malodor counteractant agent with the melted gum base; and
(4) forming the mixture from step (C) into suitable shapes.

The malodor counteractant composition is prepared according to the method of the present invention.

Another important aspect of the present invention includes a confectionery composition incorporating the inventive malodor counteractant agent and a method for preparing the confectionery compositions. The preparation of confectionery formulations is historically well known and has changed little through the years. Confectionery items have been classified as either "hard" confectionery or "soft" confectionery. The malodor counteractant agents of the present invention can be incorporated into the confections by admixing the inventive composition into the conventional hard and soft confections.

Hard confectionery may be processed and formulated by conventional means. In general, a hard confectionery has a base composed of a mixture of sugar and other carbohydrate bulking agents kept in an amorphous or glassy condition. The hard confectionery may also be sugarless. This form is considered a solid syrup of sugars generally having from about 0.5% to about 1.5% moisture. Such materials normally contain up to about 92% sugar, up to about 55% corn syrup and from about 0.1% to about 5% water, by weight of the final composition. The syrup component is generally prepared from sucrose and corn syrups, but may include other materials. Further ingredients such as flavorings, sweetening agents, acidulants, colorants and so forth may also be added.

Such confectionery may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavoring agent, colorants and the like.

A high-speed atmospheric cooker uses a heat-exchanger surface which involves spreading a film of candy on a heat exchange surface, the candy is heated to 165° C. to 170° C. in a few seconds. The candy is then rapidly cooled to 100° C. to 120° C. and worked as a plastic-like mass enabling incorporation of the additives, such as flavoring agent, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavoring agent, colorants, and other additives are admixed in the mass by routine mechanical mixing operations.

The optimum mixing required to uniformly mix the flavoring agent, colorants and other additives during conventional manufacturing of hard confectionery is determined by the time needed to obtain a uniform distribution of the materials. Normally, mixing times of from 2 to 10 minutes have been found to be acceptable.

Once the candy mass has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms: Tablets, Volume 1 (1989), Marcel Dekker, Inc., New York, N.Y. at pages 419 to 582, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particular materials and are formed into structures under pressure. These confections generally contain sugars in amounts up to about 95%, by weight of the composition, and typical tablet excipients such as binders and lubricants as well as flavoring agent, colorants and so forth. These confections may also be sugarless.

Similar to hard confectionery, soft confectionery may be utilized in this invention. The preparation of soft confections, such as nougat, involves conventional methods, such as the combination of two primary components, namely (1) a high boiling syrup such as a corn syrup, or the like, and (2) a relatively light textured frappe, generally prepared from egg albumin, gum arabic, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent. Conventionally, the final nougat composition is prepared by the addition of the "bob syrup" to the frappe under agitation, to form the basic nougat mixture. Further ingredients such as flavoring, additional carbohydrate bulking agent, colorants, preservatives, medicaments, mixtures thereof and the like may be added thereafter also under agitation. Soft confectioneries may also be prepared sugarless. A general discussion of the composition and preparation of nougat confections may be found in B. W. Minifie, Chocolate, Cocoa and Confectionery: Science and Technology, 2nd edition, AVI Publishing Co., Inc., Westport, Conn. (1983), at pages 576–580, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavor may be added. The mixture is further mixed for an additional period until it is ready to be removed and formed into suitable confectionery shapes.

In accordance with this invention, organoleptically effective amounts of the malodor counteractant agents of the present invention may be admixed into the hard and soft confections. The exact amount of malodor counteractant agent employed is normally a matter of preference subject to such factors as the particular type of confection being prepared, the type of bulking agent or carrier employed, the type of flavor employed and the intensity of breath freshening perception desired. Thus, the amount of malodor counteractant agent may be varied in order to obtain the result desired in the final product and such variations are within the capabilities of those skilled in the art without the need for undue experimentation. In general, the amount of malodor counteractant agent normally present in a hard or soft confection will be from about 0.01% to about 2%, preferably from about 0.1% to about 2%, and more preferably from about 0.25% to about 2%, by weight of the confection.

In a preferred embodiment, the present invention is directed to a confectionery composition comprising:
(i) a confectionery bulking agent; and
(ii) an organoleptically effective amount of a malodor counteractant agent selected from the group consisting of:
(A) amyl cinnamic aldehyde, benzyl benzoate, L-citronellol, citronellyl butyrate, citronellyl isobutyrate, cyclamen aldehyde, dimethyl benzyl carbinol, dimethyl benzyl carbinyl acetate, ethyl acetoacetate, geranyl butyrate, geranyl isovalerate, hexyl cinnamic aldehyde, hexyl cinnamic aldehyde diethyl acetal, hydroxycitronellal, isobornyl acetate, jessemal, linalyl butyrate, nerol, neryl acetate, phenyl ethyl isovalerate, vanillin;
(B) amyl cinnamic aldehyde, benzyl benzoate, citronellyl acetate, citronellyl isobutyrate, dimethyl benzyl carbinol, dimethyl benzyl carbinyl acetate, ethyl acetoacetate, eugenol, geraniol, geranyl acetate, geranyl butyrate, geranyl isovalerate, geranyl propionate, heliotropine, hexyl cinnamic aldehyde, hexyl cinnamic aldehyde diethyl acetal, jessemal, linalool, methyl dihydrojasmonate, phenyl ethyl alcohol; and
(C) amyl cinnamic aldehyde, benzyl benzoate, L-citronellol, citronellyl acetate, citronellyl butyrate, citronellyl isobutyrate, cyclamen aldehyde, dimethyl benzyl carbinyl acetate, geranyl butyrate, geranyl isovalerate, heliotropine, hexyl cinnamic aldehyde, hydroxycitronellal, jessemal, methyl dihydrojasmonate, nerol, vanillin.

The present invention extends to methods for making the improved confections. The malodor counteractant agents may be incorporated into an otherwise conventional hard or soft confection composition using standard techniques and equipment known to those skilled in the art. The apparatus useful in accordance with the present invention comprises mixing and heating apparatus well known in the confectionery manufacturing arts, and therefore the selection of the specific apparatus will be apparent to the artisan.

In such a method, a composition is made by admixing the inventive malodor counteractant agent into the confectionery composition along with the other ingredients of the final desired composition. Other ingredients will usually be incorporated into the composition as dictated by the nature of the desired composition as well known by those having ordinary skill in the art. The ultimate confectionery compositions are readily prepared using methods generally known in the food technology and pharmaceutical arts. Thereafter the confectionery mixture may be formed into desirable confectionery shapes.

The malodor counteractant agents may be formulated with conventional ingredients which offer a variety of textures to suit particular applications. Such ingredients may be in the form of hard and soft confections, tablets, toffee, nougat, chewy candy, chewing gum and so forth, center filled candies, both sugar and sugarless. The acceptable ingredients may be selected from a wide range of materials. Without being limited thereto, such materials include diluents, binders and adhesives, lubricants, disintegrants, bulking agents, humectants and buffers and adsorbents. The preparation of such confections and chewing gum products is well known.

The malodor counteractant compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as butylated hydroxyanisole (BHA), butylated hydroxytoluene (BHT), benzoic acid, ascorbic acid, methyl paraben, propyl paraben, tocopherols, and the like, and mixtures thereof. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gum(s), gelatin, acacia, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.01% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These colorants are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10%, and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the malodor counteractant agent with the thickener-water admixture to form a uniform thickener-malodor counteractant agent;

(D) combine the sweetener solution with the thickener-malodor counteractant agent and mix until uniform; and (E) admix the optional adjunct materials such as coloring agents, flavoring agents, decolorants, solubilizers, antifoaming agents, buffers and additional water with the mixture of step (D) to form the suspension.

The malodor counteractant compositions of this invention may also be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable malodor counteractanting candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The composition of the instant invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, *Pharmaceutical Dosage Forms: Tablets* Volume 1, Marcel Dekker, Inc., New York, N.Y. (1989) at pages 367 to 418, which disclosure is incorporated herein by reference.

In accordance with this invention, organoleptically effective amounts of the malodor counteractant agents of the present invention may be admixed into the hard and soft confectionery products. These amounts are readily determined by those skilled in the art without the need for undue experimentation. In a preferred embodiment, the malodor counteractant composition will comprise the malodor counteractant agent in an amount from about 0.25% to about 2% and an ingestible vehicle, that is a pharmaceutically acceptable carrier, in a quantity sufficient to bring the total amount of composition to 100%, by weight the ingestible malodor counteractanting composition. In a more preferred embodiment, the composition will comprise the malodor counteractant agent in an amount from about 0.05% to about 1% and an ingestible vehicle in a quantity sufficient to bring the total amount of composition to 100%, by weight the ingestible malodor counteractanting composition.

In another form of the invention, the malodor counteractant agent is incorporated into an oral topical vehicle which may be in the form of a mouthwash, rinse, oral spray, suspension, dental gel, and the like. Typical non-toxic oral vehicles known in the pharmaceutical arts may be used in the present invention. The preferred oral vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

The oral topical malodor counteractant compositions may also contain conventional additives normally employed in those products. Conventional additives include a fluorine providing compound, a sweetening agent, a flavoring agent, a coloring agent, a humectant, a buffer, and an emulsifier, providing the additives do not interfere with the malodor counteractanting properties of the composition.

The coloring agents and humectants, and the amounts of these additives to be employed, set out above, may be used in the oral topical malodor counteractanting composition.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and di-fluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the present oral topical malodor counteractanting composition is dependent upon the type of fluorine providing compound employed, the solubility of the fluorine compound, and the nature of the final oral malodor counteractanting composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the oral topical malodor counteractanting composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof. Without being limited to particular sweetening agents, representative categories and examples include:

(a) water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalacto-sucrose derivatives include but are not limited to: 1-chloro-1'-deoxysucrose; 4-chloro-4-deoxy-alpha-D-galacto-pyranosyl-alpha-D-fructofuranoside, or 4-chloro-4-deoxygalactosucrose; 4-chloro-4-deoxy-alpha-D-galacto-pyranosyl-1-chloro-1-deoxy-beta-D-fructo-furanoside, or 4,1'-dichloro-4,1'-dideoxygalactosucrose; 1',6'-dichloro-1',6'-dideoxysucrose; 4-chloro-4-deoxy-alpha-D-galacto-pyranosyl-1,6-dichloro-1,6-dideoxy-beta-D-fructo-furanoside, or 4,1',6'-trichloro-4,1',6'-trideoxygalacto-sucrose; 4,6-dichloro-4,6-dideoxy-alpha-D-galacto-pyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galacto-pyranosyl-1,6-dichloro-1,6-di-deoxy-beta-D-fructofuranoside, or 4,6,1',6'-tetrachloro-4,6,1',6'-tetradeoxygalacto-sucrose; and 4,6,1',6'-tetrachloro-4,6,1',6'-tetradeoxy-sucrose; and (e) protein based sweeteners such as *Thaumatococcous danielli* (Thaumatin I and II).

In general, an effective amount of sweetening agent is utilized to provide the level of sweetness desired in the particular oral topical malodor counteractanting composition, and this amount will vary with the sweetener selected and the final oral malodor counteractanting product desired. The amount of sweetener normally present is in the range from about 0.0025% to about 90%, by weight of the oral topical malodor counteractanting composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the oral topical malodor counteractanting composition is normally a matter of preference subject to such factors as the type of final oral malodor counteractanting composition, the individual flavor employed, and the strength of flavor desired. Thus, the amount of flavoring may be varied in order to obtain the result desired in the final product and such variations are within the capabilities of those skilled in the art without the need for undue experimentation. The flavoring agents, when used, are generally utilized in amounts that may, for example, range in amounts from about 0.05% to about 6%, by weight of the oral topical malodor counteractanting composition.

Suitable buffer solutions useful in the non-oral topical malodor counteractant compositions include citric acid-sodium citrate solution, phosphoric acid-sodium phosphate solution, and acetic acid-sodium acetate solution in amounts up to about 1%, and preferably from about 0.05% to about 0.5% by weight of the oral topical malodor counteractanting composition.

In accordance with this invention, organoleptically effective amounts of the malodor counteractant agents of the present invention may be admixed with an oral topical vehicle to form a topical malodor counteractanting composition. These amounts are readily determined by those skilled in the art without the need for undue experimentation. In a preferred embodiment, the oral topical malodor counteractant compositions will comprise the malodor counteractant agent in an amount from about 0.025% to about 2% and an oral topical vehicle in a quantity sufficient to bring the total amount of composition to 100%, by weight of the oral topical malodor counteractanting composition. In a more preferred embodiment, the oral topical malodor counteractant compositions will comprise the malodor counteractant agent in an amount from about 0.05% to about 1% and an oral topical vehicle in a quantity sufficient to bring the total amount of composition to 100%, by weight of the oral topical malodor counteractanting composition.

The present invention extends to methods for preparing the oral topical malodor counteractant compositions. In such a method, the oral topical malodor counteractanting composition is prepared by admixing an organoleptically effective amount of the malodor counteractant agent of the present invention and an oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In a preferred embodiment, an oral topical malodor counteractanting composition is made by first dissolving coloring agents, sweetening agents, and similar additives in water. The malodor counteractant agent is then admixed with the aqueous solution. Then sufficient water or ethanol, or mixtures of water and ethanol, are added to the solution with mixing until the final solution volume is reached. In a more preferred embodiment, the malodor counteractant agent is added to the solution as the final ingredient. The final oral topical malodor counteractant compositions are readily prepared using methods generally known in the pharmaceutical arts.

The oral malodor counteractanting composition may also be in the form of dental gel. As used herein, the term "gel" means a solid or semisolid colloid which contains considerable quantities of water. The colloid particles in a gel are linked together in a coherent meshwork which immobilizes the water contained inside the meshwork.

The dental gel compositions of the present invention may contain the conventional additives set out above for oral topical malodor counteractant compositions such as mouthwashes, rinses, oral sprays, and suspensions and, in addition, may contain additional additives such as a polishing agent, a desensitizing agent, and the like, providing the additional additives do not interfere with the malodor counteractanting properties of the composition.

In a dental gel composition, the oral vehicle generally comprises water, typically in an amount from about 10% to about 90%, by weight of the dental gel composition. Polyethylene glycol, propylene glycol, glycerin, and mixtures thereof may also be present in the vehicle as humectants or binders in amounts from about 18% to about 30%, by weight of the dental gel composition. Particularly preferred oral vehicles comprise mixtures of water with polyethylene glycol or water with glycerin and polypropylene glycol.

The dental gels of the present invention include a gelling agent (thickening agent) such as a natural or synthetic gum or gelatin. Gelling agents such as hydroxyethyl cellulose, methyl cellulose, glycerin, carboxypolymethylene, and gelatin and the like, and mixtures thereof may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 1%, by weight, and sodium citrate may be used in an amount from about 0.3% to about 9%, and preferably from about 0.6% to about 3%, by weight of the dental gel composition.

In accordance with this invention, organoleptically effective amounts of the malodor counteractant agents of the present invention may be admixed into the dental gel compositions. These amounts are readily determined by those skilled in the art without the need for undue experimentation. In a preferred embodiment, the dental gel compositions will comprise the malodor counteractant agent in an amount from about 0.025% to about 2% and an oral topical vehicle in a quantity sufficient to bring the total amount of composition to 100%, by weight of the dental gel composition. In a more preferred embodiment, the dental gel compositions will comprise the malodor counteractant agent in an amount from about 0.05% to about 1% and an oral topical vehicle in a quantity sufficient to bring the total amount of composition to 100%, by weight of the dental gel composition.

The present invention extends to methods for preparing the stabilized malodor counteractanting dental gel compositions. In such a method, the dental gel composition is prepared by admixing an organoleptically effective amount of the malodor counteractant agent of the present invention and an oral topical vehicle. The final compositions are readily prepared using methods generally known by those skilled in the dental and pharmaceutical arts. The apparatus useful in accordance with the present invention comprises mixing apparatus well known in the pharmaceutical arts, and therefore the selection of the specific apparatus will be apparent to the artisan.

In a preferred embodiment, an malodor counteractanting dental gel composition is made by first dispersing a gelling agent in a humectant or water, or a mixture of both, then admixing to the dispersion an aqueous solution of the water-soluble additives such as the fluorine providing compound, sweeteners and the like, then adding the polishing agent, and lastly admixing the flavoring agent and the malodor counteractant agent. The final gel mixture is then tubed or otherwise packaged. The liquids and solids in a gel product are proportioned to form a creamy or gelled mass which is extrudable from a pressurized container or from a collapsible tube. The final malodor counteractant compositions are readily prepared using methods generally known in the pharmaceutical arts.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLE 1

This example summarizes the olfactometer testing results using malodor counteractant agents to treat morning breath. The first area summarized is the background testing on the individual, mixed sulfur materials, peppermint oil, and the malodor counteractant agents. The second area summarized is the efficacy testing. All olfactometer concentration levels are given in ppb (parts per billion) and are on a volume/volume basis.

Background Testing Of Sulfur Materials And Flavors

The literature threshold for hydrogen sulfide is 18 ppb (reference: Standardized Human Olfactory Thresholds by M. Devos et. al., IRL Press at Oxford University Press, 1990). In the olfactometer tests, hydrogen sulfide was readily detectable and recognizable at 30–50 ppb, but not at 10 ppb. The literature threshold for methyl mercaptan is 1 ppb. In the olfactometer tests, it was readily apparent at 10 ppb but not at the literature threshold of 1 ppb.

A 50:50 mix (weight basis) of methyl mercaptan and hydrogen sulfide was tested at 1, 10, and 100 ppb of total sulfur. The lowest concentration was barely detectable. The 10 ppb level was easily detectable, reasonably unpleasant, and noticeably different from methyl mercaptan alone. This concentration was chosen for counteractancy testing of the flavor materials. The 100 ppb level was very unpleasant. The detection of the mixture is consistent with the thresholds and findings of the individual sulfur materials.

The initial testing of the peppermint oil, and the counteractants, counteractant CA-1A and counteractant CA-1B were done alone and in binary combinations with the sulfur mix. The counteractants had the compositions set out below.

| Counteractant CA-1A | |
|---|---|
| Ingredient Name | %, by weight |
| Benzyl Benzoate | 30.00 |
| Neryl Acetate | 7.50 |
| Trimethyl(2,6,6) Vinyl(6) Tetrahydropyran | 0.10 |
| Citronella Oil | 0.10 |
| Ethyl Alcohol | 62.30 |
| Total | 100.00 |

| Counteractant CA-1B | |
|---|---|
| Ingredient Name | %, by weight |
| Benzyl Benzoate | 30.00 |
| Neryl Acetate | 7.00 |
| Citronellyl Acetate | 0.10 |
| Geranyl Acetate | 0.10 |
| Alpha Ionone | 0.10 |
| Geranyl Propionate | 0.05 |
| Linalool | 0.02 |
| Ethyl Alcohol | 62.63 |
| Total | 100.00 |

Levels of 100 ppb for all three flavor materials were detectable but not overwhelming. All three flavor formulations modified the 10 ppb sulfur mix (synthetic mouth odor) at these levels. Most panelists noted the peppermint oil acted as a mask because both the peppermint oil and the mouth odor were apparent as separate, individually recognizable entities.

Comparing the above materials at 100 ppb is not representative of the composition in tablets because the level of peppermint oil in tablets is much higher than the level of counteractant. The CA-1A counteractant was mixed with the peppermint oil at ratios equivalent to ones that had been tested in tablets. Those tablets had been formulated with 2800 ppm of peppermint oil and 200, 400, or 600 ppm of counteractant flavor. Tests were run with 140 ppb of peppermint oil mixed with 10, 20, or 30 ppb of counteractant CA-1A flavor. The peppermint oil and CA-1A counteractant were introduced into the olfactometer through separate streams for this experiment. The lowest concentration level had little or no effect on the peppermint character, the intermediate concentration level was noticeable, and the high concentration level had a considerable impact on the peppermint character. These results are consistent with the findings using tablets.

An experiment (2 subjects, 4 judges) was run to evaluate whether the level of peppermint oil selected for the olfactometer testing relates to what is found in expired breath air with a tablet in the mouth. This was done by sensory evaluation, not analytical measurements. Peppermint oil levels were set at 40, 100, and 300 ppb. Two subjects placed standard peppermint CERTS™ tablets in their mouths. No attempts were made to evaluate the subjects prior to this test, or to have them refrain from normal eating, drinking, and oral hygiene practices. After five minutes, with tablets still in the subject's mouths, the judges evaluated the peppermint intensity of the three oil levels and of the two subjects. The intensity rating of the 100 ppb peppermint, the concentration that was used for the tests, fell between the intensity ratings for the two subjects. The oil was rated at 2.1 (40 ppb), 5.0 (100 ppb), and 6.6 (300 ppb) on a scale of 1 to 9. The two subjects were rated at 3.2 and 5.9. All judges remarked that in one subject (intensity 3.2) there was a neutral odor that largely obscured the peppermint oil, while the peppermint oil was all that was perceived in the other subject's breath. On the basis of this, it was determined that 100 ppb is appropriate for testing these flavor formulations.

Flavor Efficacy Testing

Several tests were run to determine the efficacy of the various flavor formulations. These included peppermint oil, peppermint oil with CA-1A counteractant, peppermint oil+ CA-1A counteractant+menthol (M), and peppermint oil+ CA-1A counteractant+enhancer. For the latter, two enhancers were used, which will be referred to as enhancer 2 (E2) and enhancer 7 (E7). The compositions of enhancer 2 (E2) and enhancer 7 (E7) are set out below.

| Enhancer 2 (E2) | |
|---|---|
| Component | Amount % |
| Peppermint Oil Terpeneless | 99.0000 |
| Amyl-Iso-Valerate | 0.0100 |
| Menthone | 0.0500 |
| Menthyl Acetate Laevo | 0.0270 |
| Menthol Chinese | 0.0015 |
| Ethyl Alcohol (190 PRF) | 0.4115 |
| Eromenth | 0.5000 |
| Total | 100 |

| Enhancer 7 (E7) | |
|---|---|
| Component | Amount % |
| Peppermint Oil Terpeneless | 99.1900 |
| Amyl-Iso-Valerate | 0.0040 |
| Menthone | 0.0200 |
| Menthyl Acetate Laevo | 0.0108 |
| Menthol Chinese | 0.3006 |
| Ethyl Alcohol (190 PRF) | 0.1646 |
| Eromenth | 0.3000 |
| Menthyl Chavicol | 0.0100 |
| Total | 100 |

The flavor formulations were pre-blended and introduced into the olfactometer as the blend. In the flavor formulation efficacy tests, the following category scale was used: range 1 to 9, with 1 referring to pleasant, 5 equivalent to neutral, and 9 labeled as unpleasant.

Order effects are common in sensory testing. Instead of conducting an extensive program with randomization or counter-balanced tests, a smaller series was run in which all samples were presented in a consistent order. Four samples (ports 1–4) were presented in each test, each containing the same level of synthetic mouth odor (10 ppb of sulfur mix). The first port was always the synthetic mouth odor alone. The second port was always the target level of flavor (100 ppb). Ports 3 and 4 were lower levels of flavor (40 and 20 ppb, respectively). Initially, a quantity of 100 ppb of total flavor was used. Thereafter, the method was adjusted to use 100 ppb of peppermint oil to keep the comparison consistent with product composition containing additional flavor (counteractant), not constant level of total flavoring materials. The panel results indicated with an asterisk are about 12% lower in peppermint oil than the other tests.

Table 1 shows the results of the olfactometer tests. All ratings of mouth odor without added flavor were about 7.0 (moderately unpleasant). All high (100 ppb) levels of peppermint formulations improved the perceived odor toward neutral (5.0) or pleasant ratings. Subsequent lower levels of the flavors, ports three and four, moved back toward the original unpleasant ratings. A comparison of the 100 ppb responses give the best indication of product efficacy. The peppermint oil with CA-1A counteractant did better than peppermint oil alone. Addition of menthol or either of the two enhancers to the peppermint oil with CA-1A appeared to reduce the efficacy of the counteractant.

TABLE 1

Efficacy Testing Of Peppermint Oil Flavor With Counteractant And Enhancers

| Flavor | Panel Size | Mouth Odor | Peppermint Oil Level | | |
|---|---|---|---|---|---|
| | | | 100 ppb | 40 ppb | 20 ppb |
| P* | 5 | 6.8 | 4.9 | 6.6 | 6.9 |
| P | 6 | 7.3 | 5.1 | 6.0 | 6.0 |
| P* + CA-1A | 7 | 7.2 | 3.9 | 6.2 | 6.4 |
| P + CA-1A | 4 | 7.7 | 3.5 | 5.8 | 5.8 |
| P* + CA-1A + M | 7 | 6.9 | 5.1 | 6.5 | 6.5 |
| P + CA-1A + M | 6 | 7.0 | 5.0 | 5.9 | 5.9 |
| P + CA-1A + E2 | 6 | 7.0 | 4.5 | 5.8 | 6.4 |
| P + CA-1A + E2 | 4 | 7.9 | 5.1 | 5.9 | 6.6 |
| P* + CA-1A + E7 | 6 | 7.0 | 5.7 | 6.3 | 6.7 |
| P + CA-1A + E7 | 4 | 7.6 | 4.2 | 5.1 | 6.1 |
| P + CA-1A + E7 | 6 | 6.9 | 4.9 | 6.2 | 6.3 |

P = Peppermint oil.
M = Menthol.
*Total flavor level was set at 100 ppb. Peppermint oil level was set at 88 ppb.

Conclusions

The results obtained with the olfactometer exemplify the difference between odor masking and counteractancy, and illustrate the utility of malodor counteractant compositions. These results also demonstrate the utility of the olfactometer for delivering known concentrations of odorous materials under conditions that are representative of those likely to be encountered during actual product use by consumers.

EXAMPLE 2

This example summarizes the analytical results obtained on the amount of malodor counteractant agent found in chewed and unchewed gum samples.

The following chewed and unchewed gum samples were submitted for analysis. The composition of counteractant CA-1A is set out above in Example 1.

| Identification | Day | Subject | Gum | % CA-1A |
|---|---|---|---|---|
| 1 6 D | 1 | 6 | D | 0.50 |
| 4-5-D | 4 | 5 | D | 0.50 |
| 1-3-G | 1 | 3 | G | 0.50 |
| 4-4-G | 4 | 4 | G | 0.50 |
| 1-5-E | 1 | 5 | E | 1.00 |
| 3-4-E | 3 | 4 | E | 1.00 |
| 2-6-H | 2 | 6 | H | 1.00 |
| 3-3-H | 3 | 3 | H | 1.00 |
| 2-5-F | 2 | 5 | F | 1.50 |
| 4-3-F | 4 | 3 | F | 1.50 |
| 2-4-1 | 2 | 4 | I | 1.50 |
| 3-6-J | 3 | 6 | J | 1.50 |
| D–G unchewed | | | D–G | 0.50 |
| E–H unchewed | | | E–H | 1.00 |
| F–I–J unchewed | | | F–I–J | 1.50 |

The twelve chewed gums were received with the indicated identification marked on the individual sample flasks. The exact initial (unchewed) weights were not supplied with the chewed samples. Unchewed samples were received several days later as sticks having initial weights between approximately 1600 mg and 2100 mg. The twelve chewed samples were chewed for ten minutes on four different days by four different subjects. The chewed samples were collected in 125 ml flasks, stoppered with plastic stoppers and refrigerated until shipped for analysis. Gum samples D and G have the same counteractant loading of 0.5% based on the unchewed material. Gum samples E and H both have 1.0% loading and samples F, I, and J all have 1.5% loading. The chewed and unchewed samples with the same letter designation are from the same lot.

Method Of Analysis

The gum samples were extracted into methylene chloride from a 1:1 water-methylene chloride mixture and analyzed by gas chromatography following standard methods for quantification of flavoring materials in the chewing gum. The method was modified by using split injection with approximately 10:1 split instead of a splitless injection and a temperature program of 35 degrees C.° (held for 4 min), 20 degrees C.°/min to 70 degrees C.°, then 4 degrees C.°/min to 230 degrees C.° (held for 20 min). The column used was a J & W 60 meter×0.32 mm Carbowax capillary with a 0.25 film thickness. The injector and detector temperatures were 220 and 250° C., respectively. All analysis results were corrected for the flavor carrier (ethanol). Complete extraction of all components into the methylene chloride was assumed.

Results

Table 2 shows the results for the weight percent of CA-1A in the chewed gum samples. There are twelve samples in Table 2, the last two entries being a single sample divided in half with each half being analyzed separately. The percent of CA-1A formulated into the initial gum is listed for each sample in the second column. The measured percent CA-1A is shown for the same samples in the third column. The measured values are based on the final weights of the chewed gum which are listed in the last column. The initial weights of gum sticks were not measured before chewing, but similar unchewed gum sticks were measured and found to vary between approximately 1600 mg and 2100 mg.

Table 3 shows results for the weight percent of CA-1A in unchewed gum sticks. The measured levels of CA-1A range between 56 and 130% of the expected values. The results for the triplicate analysis of E–H appear to indicate that some method variability exists.

Conclusion

After ten minutes of chewing, the gum samples retained a significant portion of the formulated level of CA-1A. The initial (unchewed) weights of the gum samples are required for an exact determination of CA-1A chew out.

TABLE 2

CA-1A in Chewed Gum

| Flask Identification | Formulated % CA-1A | Measured % CA-1A | Weight mg Chewed gum |
|---|---|---|---|
| 1-6-D-0.5% (5/11) | 0.50 | 0.68 | 878.2 |
| 4-5-D-0.5% (5/17) | 0.50 | 0.76 | 871.3 |
| 1-3-G-0.5% (5/11) | 0.50 | 0.40 | 866.8 |
| 4-4-G-0.5% (5/17) | 0.50 | 0.74 | 893.6 |
| 1-5-E-1.0% (5/11) | 1.00 | 1.89 | 695.3 |
| 3-4-E-1.0% (5/12) | 1.00 | 1.23 | 700.5 |
| 2-6-H-1.0% (5/12) | 1.00 | 1.76 | 749.2 |
| 3-3-H-1.0% (5/12) | 1.00 | 1.11 | 724.5 |

TABLE 2-continued

CA-1A in Chewed Gum

| Flask Identification | Formulated % CA-1A | Measured % CA-1A | Weight mg Chewed gum |
|---|---|---|---|
| 2-5-F-1.5% (5/12) | 1.50 | 2.42 | 852.6 |
| 2-4-I-1.5% (5/12) | 1.50 | 2.16 | 846.7 |
| 3-6-J-1.5% (5/12) | 1.50 | 1.07 | 850.7 |
| 4-3-F-1.5% (5/12) | 1.50 | 2.07 | 420.6 |
| 4-3-F-1.5% (5/12) | 1.50 | 2.03 | 447.9 |

\* Formulated CA-1A based on the initial unchewed gum weight.
\*\* Measured CA-1A based on the final chewed weight of sample. Weight loss on chewing is on the order of 50–60% of the initial stick weight.

TABLE 3

CA-1A in Unchewed Gum

| Flask Identification | Formulated % CA-1A | Measured % CA-1A | Weight mg Chewed gum |
|---|---|---|---|
| D–G | 0.50 | 0.28 | 2181 |
| E–H | 1.00 | 1.44 | 1619 |
| E–H | 1.00 | 0.91 | 1875 |
| E–H | 1.00 | 1.37 | 1866 |
| F–I–J | 1.50 | 1.95 | 2068 |

EXAMPLE 3

The following example illustrates the preparation and formulation of various compositions containing a malodor counteractant of the present invention.

| Chewing gum | |
|---|---|
| Sugar type-typical formula | % w/w |
| Gum base | 21.17 |
| Corn syrup | 16.00 |
| Sugar | 62.00 |
| Flavor | 0.80 |
| Malodor Counteractant | 0.03 to 0.1 |
| Color | Q.S. |
| | 100 00 |

Procedure a. In mixing kettle with sigma type blade, melt gum base.

b. Add corn syrup.

c. Add sugar.

d. Add flavor, color, malodor counteractant.

e. Extrude mix and pass through sizing rollers. Cut into pieces, condition to firm up and wrap.

| Sugarless type-typical formula | % w/w |
|---|---|
| Gum base | 23.90 |
| Sorbitol | 47.00 |
| Mannitol | 22.00 |

| Sugarless type-typical formula | % w/w |
|---|---|
| Glycerin | 6.00 |
| Saccharin sodium | 0.07 |
| Flavor | 1.00 |
| Malodor Counteractant | 0.03 to 0.1 |
| Color | Q.S. |
| | 100 |

Procedure a. In mixing kettle with sigma type blade, melt gum base.
b. Add sorbitol.
c. Add mannitol.
d. Add glycerin, flavor, color, malodor counteractant.
e. Extrude mix and pass through sizing rollers. Cut into pieces, condition to firm up and wrap.

Mints-Compressed Tablet

| Sugar type-typical formula | % w/w |
|---|---|
| Sugar | 95.67 |
| Corn syrup | 3.00 |
| Flavor | 0.30 |
| Malodor Counteractant | 0.03 to 0.1 |
| Color | Q.S. |
| Magnesium stearate | 1.00 |
| | 100.00 |

Procedure a. Dissolve corn syrup in sufficient water to wet the sugar.
b. Pass wet mix through a screen and dry to approximately 0.5% moisture.
c. Reduce particle size of dried mix by milling.
d. Add flavor, color, malodor counteractant.
e. Add magnesium stearate.
f. Compress final mix into tablets using a suitable tablet press.

| Sugarless type-typical formula | % w/w |
|---|---|
| Sorbitol tabletting grade | 98.67 |
| Flavor | 0.30 |
| Malodor Counteractant | 0.03 to 0.1 |
| Color | Q.S. |
| Magnesium stearate | 1.00 |
| | 100.00 |

Procedure a. In a suitable mixer, add sorbitol.
b. Add flavor, color, malodor counteractant.
c. Add magnesium stearate.
d. Compress final mix into tablets using a suitable tablet press.

Mouthwash

| Alcohol type-typical formula | % w/w |
|---|---|
| Alcohol | 28.00 |
| Benzoic acid | 0.15 |
| Eucalyptol | 0.09 |
| Menthol | 0.04 |
| Methyl salicylate | 0.06 |
| Pluronic, surfactant | 0.10 |
| Thymol | 0.06 |
| Malodor Counteractant | 0.03 to 0.1 |
| Color | Q.S. |
| Water | Q.S. to 100 ml |

Procedure a. Dissolve all ingredients in alcohol.
b. Add most of the water.
c. Adjust pH with dilute HCl to approx. 4.5.
d. Add remainder of water to make 100 ml.

| Non-Alcohol type-typical formula | % w/w |
|---|---|
| Benzoate sodium | 0.20 |
| Benzoic acid | 0.02 |
| Eucalyptol | 0.09 |
| Glycerin | 10 |
| Menthol | 0.04 |
| Methyl Salicylate | 0.06 |
| Pluronic, surfactant | 0.40 |
| Saccharin sodium | 0.06 |
| Sodium benzoate | 0.20 |
| Sodium lauryl sulfate | 0.20 |
| Thymol | 0.06 |
| Zinc chloride | 0.01 |
| Malodor Counteractant | 0.03 to 0.1 |
| Color | Q.S. |
| Water | Q.S. to 100 ml |

Procedure a. Dissolve all ingredients in ½ amount of water.
b. Add most of the water.
c. Adjust pH with benzoic acid to approx. 4.5.
d. Add remainder of water to make 100 ml.

Toothpaste

| Typical Formula | % w/w |
|---|---|
| Benzoate sodium | 0.20 |
| Cellulose gum | 0.80 |
| Dicalcium phosphate dihydrate | 88.9 |
| Flavor | 1.00 |
| Glycerin | 8.00 |
| Saccharin sodium | 0.05 |
| Sodium lauryl sulfate | 0.20 |
| Sodium monofluorophosphate | 0.76 |
| Tetrasodium pyrophosphate | 0.06 |
| Malodor Counteractant | 0.03 to 0.1 |
| Color | Q.S. |
| Water | Q.S. |
| | 100 |

| Denture Cleanser | |
|---|---|
| Tablet formula | % w/w |
| Potassium monopersulfate | 28.02 |
| Sodium borate perhydrate | 25.00 |
| Sodium carbonate | 25.00 |
| Sodium lauryl sulfoacetate | 0.50 |
| Sodium bicarbonate | 10 |
| Citric acid | 10 |
| Magnesium stearate | 0.75 |
| Flavor | 0.20 |
| Malodor Counteractant | 0.03 to 0.1 |
| Tetrasodium pyrophosphate | 0.50 |
| Color | Q.S. |
| | 100 |

EXAMPLE 4

This example illustrates the measurement of the amount of menthol and counteractants in the chewing gum released during a specified chewing period.

The chewing gums prepared are set out below.

Control—contains the mint flavor only.

Sample 1—contains the mint flavor and 3500 ppm of counteractant geranyl propionate.

Sample 2—contains the mint flavor, 1500 ppm each of counteractant geranyl propionate, and counteractant citronellyl acetate.

The chewing gums were chewed by the same subject for a duration of 1, 3, 6, 9 and 12 minutes and analyzed along with unchewed gum. The gum samples were extracted with a 1:1 NaCl saturated water/methylene-chloride mixture containing an internal standard (ethyl octanoate). The extract was filtered and injected onto the a Gas Chromatograph without concentration. The Gas Chromatograph conditions are set out below.

GC-HP-5890 with HP-7673 automatic sampler

Detector-Flame Ionization Detector

Column-OV-101 methyl silicone (Quadrex)

50 meter, 0.25 mm internal diameter, 0.25 11 film thickness.

Carrier Gas—Helium

Linear Velocity—32 cm/sec.

Oven Temp—60°–220° @3°/min., 20 min. final time

Injection Mode-Splitless

Injection Volume—1 $\mu$l

Standard Solution

Accurately weigh 0.5 grain of menthol, counteractant geranyl propionate, counteractant citronellyl acetate, and ethyl octanoate into 100 ml of methylene chloride with ethyl octanoate acting as an internal standard. Mix well. 1 ml of this stock solution was diluted into 100 ml of methylene chloride to make a final concentration of 50 mg/liter solution of these components.

Working Solution

Accurately weigh 0.2 gram of ethyl octanoate into 4 liters of methylene chloride solution and mix well. The solution should contain 50 mg/liter ethyl octanoate.

Preparation of Sample Solution

1. Weigh chewing gum before the chew and after the chew.
2. Put the chewed gum into a 250 ml Erlenmeyer flask.
3. Add 100 ml water, 50 grams salt, and 100 ml working solution.
4. Put the flask onto an Equatherm orbital shaker, set at 5, and shake it until all sample is dissolved. (about 45 minutes).
5. Pour the contents of the flask into a 500 ml separatory funnel, and allow the layers to separate for 4 hours.
6. Filter the bottom layer through sodium sulfate. Take a portion of the extract and filter it through a 0.45 $\mu$m syringe filter into an autosampler vial.

7.1 $\mu$l of each sample is injected into the GC without splitting sample.

Calculation

The percents of counteractant and menthol remaining in the chewed gum were calculated as follows:

$$(A_S/A_R) \times (V_S/W_G) \times (W_R) \times 100$$

where $A_S$=area ratio of counteractant(menthol) to internal standard in sample.

$A_R$=area ratio of counteractant (menthol) to internal standard.

$V_S$=volume of working solution in the sample flask (ml).

$W_G$=weight of unchewed chewing gum (mg).

$W_R$=weight of counteractant (menthol) in standard (mg/ml).

Results

The amount of the mint flavor, menthol and counteractants left after chewing for the specified durations were measured. The results were plotted on bar graphs (not shown) based on the weight of unchewed gum. The amount of flavor reported is expected to be much higher than the actual amount left due to the high response ratio of menthol to the internal standard. The low concentrations of counteractants resulted in an amplified effect of minor deviations. The rates of menthol and flavor release while chewing were observed to be close to each other. Both menthol and flavor release lost approximately 15–20% of the original amount after 12 minutes of chewing. Less counteractant was released during the same chewing period than menthol or the mint flavor itself.

EXAMPLE 5

This example illustrates the measurement of the amount of menthol and counteractants in a chewing gum released during a specified chewing period.

The chewing gums prepared are set out below.

Control—contains the mint flavor only.

Sample 3—contains the mint flavor and total 3500 ppm of the counteractant geranyl propionate and citronellyl acetate at the ratio of 75% /25%, respectively.

Sample 4—contains the mint flavor and total 3500 ppm of the counteractant geranyl propionate and citronellyl acetate at the ratio of 25%/75%, respectively.

Chewing gums were chewed by the same subject for a duration of 12 minutes and analyzed along with unchewed gum. The gum samples were extracted with a 1:1 NaCl saturated water/methylene-chloride mixture containing an internal standard(ethyl octanoate). The extract was filtered and injected onto the GC without concentration. Gas Chromatographic conditions were the same as set out above in Example 4.

Standard Solution

Accurately weigh 0.5 gram of menthol, counteractant geranyl propionate, counteractant citronellyl acetate, and ethyl octanoate into 100 ml of methylene chloride with ethyl octanoate acting as an internal standard. Mix well. 1 ml of this stock solution was diluted into 100 ml of methylene chloride to make a final concentration of 50 mg/liter solution of these components.

The Working Solution, the Sample Solution, and the Calculations were the same as set out above for Example 4.

An approximately a 15%–20% loss of the flavor and menthol was observed, but only a 5–10% loss of counteractants after 12 minutes of chewing was observed. This finding supports the previous 1, 3, 6, 9, and 12 minute chew-out study that release of counteractant geranyl propionate and counteractant citronellyl acetate were much slower than the menthol and mint flavor release.

EXAMPLE 6

This example illustrates a comparison of two malodor counteractant compositions versus a control studied in vitro to determine their effectiveness in reducing breath malodor.

Malodor Study—Jar Tests

Two counteractants, CA-1A and CA-1B, were studied in vitro to determine their effectiveness in reducing breath malodor. The composition of counteractants CA-1A and CA-1B are set out above in Example 1.

A Rotten Tooth Malodor Blend, a mixture of compounds reminiscent of oral decay created for research purposes, was used in jar studies as the insult treatment upon which the counteractants were added. Using trained panelists, it was determined that both counteractants significantly reduce the malodor intensity in the headspace of the jars tested. The objective of the study was to determine the efficacy of the counteractants on reducing breath malodor through in vitro studies.

Ten panelists were selected based upon their previous training, past performance, and ability to discriminate between various malodor chemicals. Three jars were presented to each panelist. Samples 1–3 consisted of the following components.

Sample 1—Control (0.02 gm of Rotten Tooth Malodor Blend).

Sample 2—Control (0.02 gm of Rotten Tooth Malodor Blend) plus Counteractant CA-1A (0.04 gm).

Sample 3—Control (0.02 gm of Rotten Tooth Malodor Blend) plus Counteractant CA-1B (0.04 gm).

Samples were blind coded with 3 digit random numbers and presented in balanced random order. Each subject received his or her own set of samples due to the volatile nature of the compounds in the jars. Tests were repeated twice. Panelists were requested to sniff each jar then rate the malodor intensity using a 7 point scale, where 1=no malodor and 7=high malodor). The results of the malodor intensity are set out below.

| Sample | Malodor Mean Intensity |
|---|---|
| 1 | 6.27 |
| 2 | 2.62 |
| 3 | 2.20 |

| Statistical Results | |
|---|---|
| | Statistic |
| Whole model test | F < 0.0001 |
| CA-1A vs. control | t < 0.0001 |
| CA-1B vs. control | t < 0.0001 |
| CA-1A vs. CA-1B | t < 0.1246 |

Accordingly, a significant difference in malodor intensity exists, at the 95% confidence interval, between the jar containing only the control and the jars containing the counteractant/control blends. No significant statistical difference was observed between the two sets of jars containing the counteractant/control blends. Hence, counteractants, CA-1A and CA-1B have a significant effect in reducing the malodor intensity in the headspace of the jars tested.

EXAMPLE 7

This example illustrates the effectiveness of a malodor counteractant composition studied in vivo to determine its effectiveness in reducing extrinsic breath malodor.

Malodor—90 Minute Study

Second Party Extrinsic Test

Counteractant CA-1B, the composition of which was set out in Example 6, was studied in vivo to determine its effectiveness in reducing extrinsic breath malodor. Second party perception tests were conducted using five pairs of trained panelists. The counteractants were evaluated in hard boiled candy for 90 minutes. Both the counteractant and placebo demonstrated an initial significant drop in malodor intensity while the candy was still in the subject's mouth. After the candy dissolved, the malodor intensity of the counteractant remained at a constant low level while the placebo demonstrated a significant increase. The objective of the study was to determine the efficacy of the counteractant CA-1B on reducing extrinsic breath malodor through in vivo studies.

In vivo studies were conducted on five pairs of panelists. The panelists were selected based upon their willingness to participate, their availability, their capacity to discriminate between the various malodors chemicals, and their previous training. Panelists were divided up into "judge and subject" pairs. The subject would be the panel member who ingested the insult and/or the counteractant. The judge would be the panel member who evaluated the subject's breath. The breath was evaluated by the subject exhaling in a steady and forceful manner towards the judge, who was less than 4 inches away. Tests were conducted between 8:30 and 10:00 AM. The panelists were asked not to eat or drink during the study. The insult treatment consisted of 0.5 gm of nacho powder seasoning (Nacho Powder #1437801 available from Bush Boake Allen, Inc., Seasoning Division, Carrollton, Tex., a food product used at 9.0% to season yellow corn chips). The powder was measured out onto a white plastic spoon. The subjects had up to one minute to ingest the powder completely. The placebo and counteractant were delivered in hard-boiled candy (2.8 gm per piece). The placebo consisted of 80 ppm of isoamyl acetate per individual candy (0.02 gm/250 gm batch). The counteractant consisted of CA-1B @0.15% plus the 80 ppm of iso amyl acetate. Judges were asked to evaluated their partner's breath, at 12 time stations: before taking the insult (time 0), followed by 1, 5, 10, 12, 14, 16, 18, 20, 30, 60, and 90 minutes after ingesting the insult. The candy was ingested immediately after taking the 5 minute intensity rating. A seven point intensity scale, where 1=no malodor and 7=exteremely high malodor). The results were analyzed using One Way Analysis of Variance Tests, Multivariate Analysis of Variance Tests, Tukey-Kramer HSD Tests, and Least Square Means, and are set out below.

Malodor Intensity Means

| Time | Baseline | Placebo | CA-1B |
| --- | --- | --- | --- |
| Before | 1.88 | 1.75 | 1.50 |
| 1 min | 7.00 | 6.75 | 6.75 |
| 5 min* | 7.00 | 6.75 | 6.88 |
| 10 min | 6.50 | 3.50 | 3.25 |
| 12 min** | 6.50 | 2.75 | 2.75 |
| 14 min | 6.50 | 3.25 | 2.88 |
| 16 min | 6.50 | 4.25 | 2.38 |
| 18 min | 6.50 | 4.25 | 2.50 |
| 20 min | 6.50 | 4.25 | 3.25 |
| 30 min | 5.75 | 5.25 | 3.00 |
| 60 min | 4.75 | 4.50 | 2.88 |
| 90 min | 4.50 | 4.50 | 2.88 |

*Candy was ingested immediately after this score was recorded.
**Candy was dissolved in all the subjects by this time station.

Analysis of Variance

| Effect | Statistic |
| --- | --- |
| Whole model test | F < 0.0001 |
| Sample | F < 0.0001 |
| Time in Minutes | F < 0.0001 |
| Sample by Time in minutes | F < 0.0001 |

Malodor Intensities Probabilities of CA-1B vs. Placebo

| Time Station | Malodor Intensity of CA-1B vs. Placebo |
| --- | --- |
| Time 0 (before insult) | t = 1.0000 |
| 1 minute | t = 1.0000 |
| 12 minutes | t = 0.4325 |
| 16 minutes | t < 0.0001 |
| 20 minutes | t = 0.0195 |
| 30 minutes | t < 0.0001 |
| 60 minutes | t = 0.0037 |
| 90 minutes | t = 0.0020 |

T Probability Comparing CA-1B Placebo with The Baseline At 90 Minutes

| Samples | t Probability at 90 Minutes |
| --- | --- |
| Baseline vs. Placebo | t = 0.6945 |
| Baseline vs. CA-1B | t = 0.0066 |

Using the pooled data, counteractant CA-1B was found to have a significantly different effect from the placebo at a 95% confidence interval. Nacho powder was used as the insult treatment because of its wide range of malodor notes and tenacity in the breath. Ingestion of this insult treatment resulted in a 5.12 mean increase in malodor intensity (7 point scale). Both the counteractant and the placebo elicited an initial 4.13 mean decrease in malodor intensity while the candy was dissolving in the subject's mouth. This effect may have been caused by the increased salvation when the candy was in the subject's mouth. The malodor intensity scores for the placebo and counteractant were the same from Time O (before insult), until the candy was completely dissolved in the subject's mouth (Time=12 minutes). After the 12 minute interval, the malodor intensity of the placebo increased sharply. In contrast, the malodor intensity of the counteractant remained low. The malodor intensity of the counteractant was significantly less than the placebo from the 16 through 90 minute time intervals. There was no significant difference between the malodor intensities of the placebo and the baseline at the 90 minute time station (t=0.6945). There was a significant difference between the counteractant and the baseline at the 90 minute time station 0=0.0066). The subjects (panelist member who ingested the candy) were requested to comment about the tastes in their mouth after each test.

(Test #2—Placebo, Test #3—Counteractant).

Mouth feels fresher with test #3 than with test #2.

No nacho remnants after candy dissolves in test #3.

No nacho taste after candy dissolves in test #3.

Mouth feel is cleaner in test #3 than in test #2.

The degree of effectiveness of the counteractant varied from individual to individual. In summary, the counteractant was effective on reducing malodor intensities in all of the five subjects for 90 minutes.

The invention being thus described, it will be obvious that the same may be varied in many ways. Such variations are not to be regarded as a departure from the spirit and scope of the invention and all such modifications are intended to be included within the scope of the following claims.

I claim:

1. A method of counteracting a malodor in the oral cavity of a mammal caused by a compound selected from the group consisting of lower carboxylic acids, thiols, thiophenols, phenols, lower amines, phosphines, and arsines, comprising introducing into the oral cavity an effective malodor counteracting amount of a malodor counteracting compound in an oral vehicle, wherein the malodor counteracting compound is selected from the group consisting of, in percentages by weight:

(A) (a) geranyl propionate in an amount from about 85% to about 99.99%; (b) benzyl benzoate in an amount from about 0.001% to about 10%; and (c) neryl acetate in an amount from about 0.001% to about 10%;

(B) (a) citronellyl acetate in an amount from about 85% to about 99.99%; (b) benzyl benzoate in an amount from about 0.001% to about 10%; and (c) neryl acetate in an amount from about 0.001% to about 10%;

(C) (a) benzyl benzoate in an amount from about 70% to about 95%; (b) geranyl propionate in an amount from about 3% to about 20%; and (c) citronellyl acetate in an amount from about 1% to about 15%;

(D) (a) geranyl propionate in an amount from about 65% to about 85%; (b) citronellyl acetate in an amount from about 10% to about 25%; and (c) benzyl benzoate in an amount from about 1% to about 15%;

(E) (a) citronellyl acetate in an amount from about 55% to about 75%; and (b) geranyl propionate in an amount from about 25% to about 45%; and whereby the perceived total odor intensity in the oral cavity is reduced and the perceived malodor intensity in the oral cavity is substantially eliminated.

2. The method according to claim 1, wherein the oral vehicle is selected from the group consisting of chewing gum compositions, hard and soft confections, mouth washes, tooth pastes, denture cleaners, and dental floss.

3. The method according to claim 2, wherein the oral vehicle is a chewing gum composition.

4. The method according to claim 2, wherein the oral vehicle is a hard or soft confection.

* * * * *